United States Patent [19]

Jentsch et al.

[11] Patent Number: 5,616,730
[45] Date of Patent: Apr. 1, 1997

[54] PROCESS FOR PREPARING SUCCINIC ANHYDRIDE

[75] Inventors: Joerg-Dietrich Jentsch, Mülheim; Georg Martin, Düsseldorf; Eberhard Zirngiebl, Köln, all of Germany

[73] Assignee: Bayer Aktiengesellschaft, Leverkusen, Germany

[21] Appl. No.: 468,586

[22] Filed: Jun. 6, 1995

[30] Foreign Application Priority Data

Jul. 8, 1994 [DE] Germany ............... 44 24 069.4

[51] Int. Cl.⁶ ............................................. C07D 307/60
[52] U.S. Cl. ............................................................ 549/233
[58] Field of Search ............................................. 549/233

[56] References Cited

FOREIGN PATENT DOCUMENTS

| | | | |
|---|---|---|---|
| 441002 | 2/1927 | Germany | 549/233 |
| 1768791 | 2/1972 | Germany | 549/233 |
| 7307609 | 3/1973 | Japan | 549/233 |
| 987326 | 3/1965 | United Kingdom | 549/233 |

OTHER PUBLICATIONS

Chemical Abstracts, vol. 103, abstract no. 6210k, abstract of CS 218083 (1984).
Chemical Abstracts, vol. 98, abstract no. 34252 (1993).
German translation of CS 195,860.
Chemical Abstracts, vol. 114, abstract no. 42561m, abstract of JP 02–000,680 (1990).
Chemical Abstracts, vol. 113, abstract no. 23679a, abstract of SU 1541210 (1990).
Chemical Abstracts, vol. 93, abstract no. 71047b, abstract of SU 721,406 (1980).
Chemical Abstracts, vol. 79, abstract no. 5013x (1973).
English translation of JP 48–7609 (1973).
Derwent Abstract of CN 1063484 Dec. 1992).

*Primary Examiner*—Bernard Dentz
*Attorney, Agent, or Firm*—Sprung Horn Kramer & Woods

[57] ABSTRACT

Succinic anhydride (SA) can be prepared by catalytic hydrogenation of maleic anhydride (MA) with hydrogen in the liquid phase, by reacting a starting material composed of from 5 to 100% by weight of MA and from 95 to 0% by weight of SA, based on the total weight of MA and SA, at from 120° to 150° C. and a $H_2$ pressure of from 10 to 150 bar over a Raney skeleton catalyst or a platinum group metal catalyst.

9 Claims, No Drawings

PROCESS FOR PREPARING SUCCINIC ANHYDRIDE

BACKGROUND OF THE INVENTION

1. Field of the Invention

The present invention relates to a process for preparing succinic anhydride (SA) by catalytic hydrogenation of maleic anhydride (MA) in the liquid phase.

SA is a valuable synthetic building block for preparing succinic acid, diesters of succinic acid, succinimides, polyesters and pharmaceuticals.

2. Description of the Related Art

It is already known that SA can be obtained by dehydration of succinic acid or by catalytic hydrogenation of maleic anhydride (MA). The catalytic hydrogenation of MA is generally carried out in the liquid phase over a suspended catalyst.

Mild reaction conditions, the co-use of a diluent, the co-use of deactivators for the catalyst and the setting of low temperatures are provided here. These mild reaction conditions quite obviously serve to suppress undesired reactions such as the polymerization of the MA or overhydrogenation, for example to give γ-butyrolactone. Thus, according to CS 218 083 (cited according to C. A. 103, 6210 k), the hydrogenation is carried out in ethyl acetate in the presence of Raney nickel which has previously been deactivated by acetic acid or by ethyl acetate.

For example, according to CS 195 860, a 1:1 mixture of MA in γ-butyrolactone is reacted over catalysts from the group consisting of copper on kieselguhr, NiO on kieselguhr, Cu—Zn—Cr catalyst or Raney copper at from 100° to 300° C. to give a reaction product containing succinic acid, γ-butyrolactone and propionic acid.

Here the $C_3$ product propanol is formed from the $C_4$ starting material MA, apparently by decarbonylation or decarboxylation.

According to JP 02/200 680 (cited according to C. A. 114, 42561 m), maleic acid or MA is reacted at 200° C. in tetraethylene glycol dimethyl ether to give γ-butyrolactone and SA; use is here made of a complicated catalyst system comprising ruthenium, organic phosphines, conjugated bases of acids having a pKa <2 and chlorine-containing compounds from the group consisting of hydrochlorides or metal chlorides.

According to SU 1 541 210 (cited according to C. A. 113, 23679 u), the reaction is carried out in acetone as solvent at from 15° to 50° C. using a Pd/activated carbon catalyst which had been modified with triethylamine. Dioxane is proposed as solvent in SU 721 406 (cited according to C. A. 93, 71047 b), which solvent contains the MA as a from 30 to 5% strength by weight solution.

The process of JP 48/07609 (1973) is carried out in the gas phase with use of a further specific measure, namely a deficiency of hydrogen (molar ratio $H_2$: MA=1:3), with, according to Example 1 of this Japanese patent application, both Pd on $Al_2O_3$ and a Ni—Re catalyst being used together as hydrogenation catalyst.

According to the process of CN 1 063 484, SA is prepared by melting MA at from 60° to 80° C. and carrying out the hydrogenation at a rising temperature of from 70° to 126° C. in the presence of a Raney nickel catalyst comprising four components (without more detailed description).

The reaction product is subsequently cooled and, after solidification, is broken up coarsely and packed. Although this process avoids the use of a solvent, it incorporates instead a complicated (not described in more detail) catalyst and the need for a complicated temperature profile which obviously follows the increasing formation of SA in the reaction mixture and, if it is not adhered to, results in SA crystallizing out and the stirrer being impeded.

SUMMARY OF THE INVENTION

It has now been found that, contrary to the prejudgements made in respect of undesired side-reactions, hydrogenation can be carried out at temperatures which are from the beginning above the melting point of SA, the desired hydrogenation reaction of the MA to give SA evidently overtaking all other competitive reactions without undesired further hydrogenations or cleavage reactions occurring. Thus, for example, only insignificant amounts of butyric acid and γ-butyrolactone are observed.

The invention accordingly provides a process for preparing succinic anhydride (SA) by catalytic hydrogenation of maleic anhydride (MA) with hydrogen in the liquid phase, which is characterized in that a starting material composed of from 5 to 100% by weight of MA and from 95 to 0% by weight of SA, based on the total weight of MA and SA, is reacted at from 120° to 150° C. and a $H_2$ pressure of from 10 to 150 bar over a hydrogenation catalyst.

DETAILED DESCRIPTION OF THE INVENTION

The process of the invention is carried out at a temperature of from 120° to 150° C., preferably at from 125° to 140° C., particularly preferably at from 127° to 135° C. An excess of hydrogen is made available. Its amount is not represented by the molar ratio, but, as is customary in hydrogenation reactions under superatmospheric pressure, by the $H_2$ pressure which is from 10 to 150 bar, preferably from 20 to 130 bar, particularly preferably from 50 to 120 bar.

The catalyst used is one which has been found to be particularly suitable for the hydrogenation of double bonds. Such a catalyst belongs to the group of Raney skeleton catalysts and the catalysts of transition groups I and VIII. In detail, mention may be made of: Raney (Ni,Co,Cu,Fe), where one or more of the hydrogenation-active metals can be present, and a catalyst containing one or more hydrogenation-active components from the transition groups I and VIII, such as Pd, Rh, Ru, Pt, Ir, Ni, Co, Fe and Cu. While Raney catalysts of the type mentioned can be used as skeleton catalysts and thus require no support, the catalysts of transition groups VIII and I can be used either as a metal powder (in the form of a catalyst slurry) or as supported catalysts. Supports for this purpose are, for example, aluminium oxides of the various structures, $SiO_2$ of the various structures, activated carbon, mixtures of aluminium oxides and $SiO_2$, titanium dioxide, barium sulphate and other inert supports known to those skilled in the art in the form of powders or shaped bodies.

Among the Raney catalysts, preference is given for cost reasons to those in which only one or two of the specified metals, particularly preferably only one of the specified metals, are (is) present. Very particular preference is given to using Raney Ni.

Among the platinum group metals, Pd or Pt is preferred; particular preference is given to Pd.

While the process of the invention can in principle also be carried out in the presence of diluents, for example of the abovementioned type, it is useful and preferred, particularly for reasons of simplicity, to carry it out completely without solvent.

In the process of the invention, a starting material composed of from 5 to 100% by weight of MA and from 95 to 0% by weight of SA, preferably 20–100% by weight of MA and 80–0% by weight of SA, is reacted. It is thus possible to react pure MA according to the invention. This can be carried out, for example, as a batch process, continuously by use of plug flow in a tube reactor or in the form of the likewise continuous trickling phase over a fixed-bed catalyst. However, the starting material can also contain SA within the composition range of the specified mixture. This process variant too can be carried out as a batch process, in plug flow or in the trickling phase over a fixed-bed catalyst.

A specific process variant which may be mentioned is the semi-batch procedure in which liquefied MA is added under hydrogenation conditions to a suspension of the catalyst in initially charged liquid SA and is hydrogenated, SA is then taken off in an amount corresponding on average (±30%) to the MA added, so that some SA remains in the reactor, and the procedure is repeated with renewed addition of MA. The amount of MA added, based on the mass of SA initially charged, can vary within wide limits, for example from 5 to 5000%, preferably from 100 to 5000%.

When using reactors having a stirring device (pressure reactors, autoclaves) and when carrying out the process continuously in a tube reactor, the catalyst is used in slurry form or in finely powdered form and is circulated, for example by slurry pumps. When using the trickling phase, but also when using plug flow in a tube reactor, the catalyst can also be used as fixed-bed catalyst, for example in pelletized and coated form. The amount of the catalyst is, calculated as catalyst metal, from 0.01 to 10% by weight, preferably from 0.05 to 8% by weight, particularly preferably from 0.1 to 5% by weight, based on the mass of MA to be reacted. In the case of a continuous or semi-batch procedure, the LHSV is from 10 to 500 g, preferably from 20 to 200 g, particularly preferably from 30 to 100 g, of MA per g of catalyst per hour.

Although it is possible in principle to vary the process temperature within the specified range while carrying out the process, it is preferred, for reasons of simplicity, to keep the temperature constant within a very narrow range in the total range. This eliminates any special temperature regulation dependent on the progress of the reaction. Furthermore, the catalyst is not exposed to any temperature fluctuations, which increases its operating life and activity.

EXAMPLE 1

200 g of SA and 12 g of Raney Ni (washed three times with methanol, three times with toluene and subsequently with liquid SA at 130° C.) were placed at room temperature in a 0.7 l V4A autoclave and melted at 130° C. under 100 bar of hydrogen. While stirring, 200 g of molten MA were subsequently pumped in over a period of 60 minutes. The mixture was subsequently stirred for a further 20 minutes, the autoclave was vented and the molten material was filtered hot from the catalyst. This gave, after cooling, 401 g of solid containing 99.4% by weight of SA. The yield, based on MA used, was 97.3% of theory.

EXAMPLE 2

200 g of SA and 6 g of Pd catalyst on aluminium oxide (5% by weight of Pd) were placed at room temperature in a 0.7 l V4A autoclave and melted at 130° C. under 100 bar of hydrogen. While stirring, 200 g of molten MA were subsequently pumped in over a period of 60 minutes. The mixture was subsequently stirred for a further 20 minutes, the autoclave was vented and the molten material was filtered hot from the catalyst. This gave, after cooling, 403 g of solid containing 99.2% by weight of SA. The yield, based on MA used, was 97.9% of theory.

EXAMPLE 3

200 g of SA and 6 g of Pd catalyst on activated carbon (5% by weight of Pd) were placed at room temperature in a 0.7 l V4A autoclave and melted at 130° C. under 100 bar of hydrogen. While stirring, 200 g of molten MA were subsequently pumped in over a period of 60 minutes. The mixture was subsequently stirred for a further 20 minutes, the autoclave was vented and the molten material was filtered hot from the catalyst. This gave, after cooling, 402 g of solid containing 99.8% by weight of SA. The yield, based on MA used, was 98.6% of theory.

EXAMPLE 4

200 g of SA and 12 g of Raney Ni (washed three times with methanol, three times with toluene and subsequently with liquid SA at 130° C.) were placed at room temperature in a 0.7 l V4A autoclave and melted at 130° C. under 100 bar of hydrogen. While stirring, 200 g of molten MA were subsequently pumped in over a period of 60 minutes. The mixture was subsequently stirred for a further 20 minutes, the stirrer was switched off and about 200 g of SA were pushed out via a riser tube containing a frit by means of the hydrogen pressure. Subsequently a further 200 g of MA were pumped in under the abovementioned conditions. A total of 1800 g of MA are used. This gave 2020 g of SA containing 99.4% by weight of SA. The yield was 98.4% of theory, based on MA used.

EXAMPLE 5

200 g of SA and 6 g of Pd catalyst on $Al_2O_3$ (5% by weight of Pd) were placed at room temperature in a 0.7 l V4A autoclave and melted at 130° C. under 100 bar of hydrogen. While stirring, 200 g of molten MA were subsequently pumped in over a period of 60 minutes. The mixture was subsequently stirred for a further 20 minutes, the stirrer was switched off and about 200 g of SA were pushed out via a riser tube containing a frit by means of the hydrogen pressure. Subsequently a further 200 g of MA were pumped in under the abovementioned conditions. A total of 2000 g of MA are pumped in. This gave 2240 g of SA containing 99.5% by weight of SA. The yield, based on MA used, was 99.4% of theory, based on MA used.

What is claimed is:

1. A process for the preparation of succinic anhydride (SA) which comprises catalytically hydrogenating in a semi-batch or continuous procedure maleic anhydride (MA) with hydrogen in the liquid phase wherein the starting material, based upon total weight of MA and SA is composed of at least 5% of MA and up to 95% SA, at a temperature of 125° C. to 140° C. and at a $H_2$ pressure from 20 to 130 bar; and wherein 0.01 to 10% by weight of catalyst, based upon MA, is initially charged with the SA.

2. The process of claim 1, wherein in a semi-batch procedure, liquid MA is added to initially charged liquid SA and is hydrogenated, SA is taken from the hydrogenation mixture in an amount corresponding on average to the amount of MA added, so that some SA remains, and the procedure is repeated with renewed addition of MA.

3. The process of claim 1, wherein the starting material is reacted continuously in the trickling phase or in a tube reactor.

4. The process of claim 1, wherein the hydrogenation catalyst is a Raney skeleton catalyst containing from 1 to 4 of the elements Ni, Co, Fe and Cu.

5. The process of claim 1, wherein the hydrogenation catalyst contains one or more hydrogenation-active components from transition groups I and VIII and is present as metal powder or as supported catalyst.

6. The process of claim 5, wherein supports may be $Al_2O_3$ of the various structures, $SiO_2$ of the various structures, mixtures of $Al_2O_3$ and $SiO_2$, activated carbon, $TiO_2$ or $BaSO_4$.

7. The process according to claim 1 wherein the catalyst is Raney Ni.

8. The process according to claim 1, wherein the catalyst is a Raney skeleton catalyst or a catalyst of transition group VIII, wherein the metal is selected from the group consisting of Pd, Rh, Ru, Pt, Ir and Fe.

9. The process according to claim 1, wherein the catalyst is a catalyst of transition groups I and VIII wherein the metal is selected from the group consisting of Pd, Rh, Ru, Pt, Ir and Fe.

* * * * *